(12) United States Patent
Cotarca et al.

(10) Patent No.: US 8,933,226 B2
(45) Date of Patent: Jan. 13, 2015

(54) PROCESS FOR PREPARING BOSENTAN MONOHYDRATE AND IT'S INTERMEDIATES

(75) Inventors: Livius Cotarca, Cervignano del Friuli (IT); Massimo Verzini, Caldiero (IT); Elisa Melotto, Lonigo (IT); Ivan Michieletto, Venice (IT); Alfonso Melloni, Verona (IT); Paolo Maragni, Virgilio (IT); Raffaella Volpicelli, Vicenza (IT); Mauro Andretto, Noventa Vicentina (IT); Corrado Colli, Galliate (IT)

(73) Assignee: Zach Systems S.p.A., Bresso (Milano) (IT)

( * ) Notice: Subject to any disclaimer, the term of this patent is extended or adjusted under 35 U.S.C. 154(b) by 0 days.

(21) Appl. No.: 13/824,620

(22) PCT Filed: Sep. 22, 2011

(86) PCT No.: PCT/EP2011/066531
§ 371 (c)(1),
(2), (4) Date: May 14, 2013

(87) PCT Pub. No.: WO2012/041764
PCT Pub. Date: Apr. 5, 2012

(65) Prior Publication Data
US 2013/0253195 A1   Sep. 26, 2013

(30) Foreign Application Priority Data
Oct. 1, 2010 (EP) ..................... 10185950

(51) Int. Cl.
*C07D 403/04*   (2006.01)
*C07D 239/69*   (2006.01)
*C07C 31/20*    (2006.01)

(52) U.S. Cl.
CPC ........... *C07D 239/69* (2013.01); *C07C 31/202* (2013.01)
USPC ........................................ 544/296

(58) Field of Classification Search
CPC ..................................... C07D 239/69
See application file for complete search history.

(56) References Cited

U.S. PATENT DOCUMENTS

2009/0156811 A1   6/2009   Taddei et al.

FOREIGN PATENT DOCUMENTS

| WO | 2009/004374 | 1/2009 |
| WO | WO 2009004374 A1 * | 1/2009 |
| WO | 2010/103362 | 9/2010 |
| WO | WO 2010103362 A2 * | 9/2010 |
| WO | 2011/058524 | 5/2011 |

OTHER PUBLICATIONS

Peter J. Harrington, et al., Research and Development of a Second-Generation Process . . . , Organic Process Research & Development, vol. 6, pp. 120-124, 2002.
Hironori Harada, et al., Ethenesulfonamide and Ethanesulfonamide Derivatives . . . , Bioorganic & Medicinal Chemistry, vol. 9, pp. 2955-2968, 2001.

* cited by examiner

*Primary Examiner* — Noble Jarrell
*Assistant Examiner* — John S Kenyon
(74) *Attorney, Agent, or Firm* — Silvia Salvadori, P.C.

(57) ABSTRACT

The present invention relates to a process for preparing Bosentan Monohydrate; in particular, the present invention provides the preparation of the novel 4-tert-butyl-N-[6-(2-hydroxy-ethoxy)-5-(2-methoxy-phenoxy)-2-(2-pyrimidinyl)-pyrimidin-4-yl]-benzenesulfonamide sodium salt as an ethylene glycol solvate (Bosentan sodium salt ethylene glycol solvate), which is a useful intermediate for obtaining Bosentan Monohydrate in a pure form.

14 Claims, 3 Drawing Sheets

PROCESS FOR PREPARING BOSENTAN MONOHYDRATE AND IT'S INTERMEDIATES

This application is a U.S. national stage of PCT/EP2011/066531 filed on Sep. 22, 2011 which claims priority to and the benefit of European Application No. 10185950.2 filed on Oct. 1, 2010, the contents of which are incorporated herein by reference.

FIELD OF THE INVENTION

The present invention relates to a process for preparing Bosentan Monohydrate. In particular, the present invention relates to the preparation of the novel 4-tert-butyl-N-[6-(2-hydroxy-ethoxy)-5-(2-methoxy-phenoxy)-2-(2-pyrimidinyl)-pyrimidin-4-yl]-benzenesulfonamide sodium salt as an ethylene glycol solvate (Bosentan sodium salt ethylene glycol solvate), which is useful for obtaining Bosentan Monohydrate in a pure form.

BACKGROUND OF THE INVENTION

Bosentan Monohydrate, the active ingredient in the drug product Tracleer®, is an endothelin receptor antagonist, belonging to a class of highly substituted pyrimidine derivatives, which has the chemical name 4-tert-butyl-N-[6-(2-hydroxy-ethoxy)-5-(2-methoxy-phenoxy)-2-(2-pyrimidinyl)-pyrimidin-4-yl]-benzenesulfonamide monohydrate and the following structural formula (I):

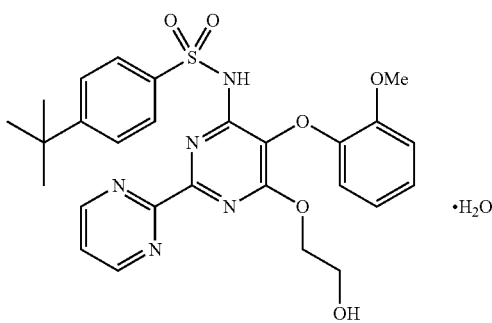

(I)

Bosentan Monohydrate was developed for treatment of pulmonary arterial hypertension.

Hoffmann La-Roche EP 526708 discloses the preparation of crude Bosentan sodium salt, which involves coupling of 4-tert-butyl-N-[6-chloro-5-(2-methoxy-phenoxy)-2-(2-pyrimidinyl)-pyrimidin-4-yl]-benzenesulfonamide and sodium ethylene glycolate in ethylene glycol as a solvent at a temperature of 100° C.

The formation of the dimer impurity of formula (Ia) and of the pyrimidinone impurity of formula (Ib)

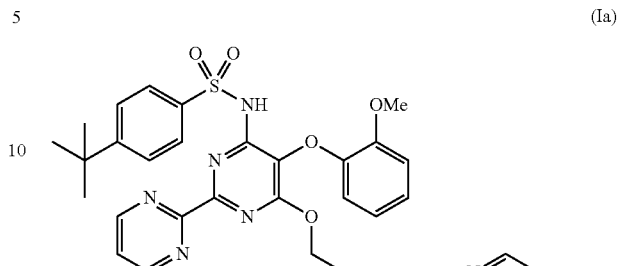

(Ia)

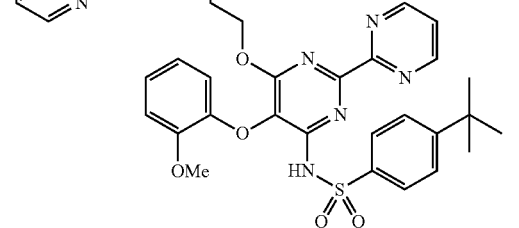

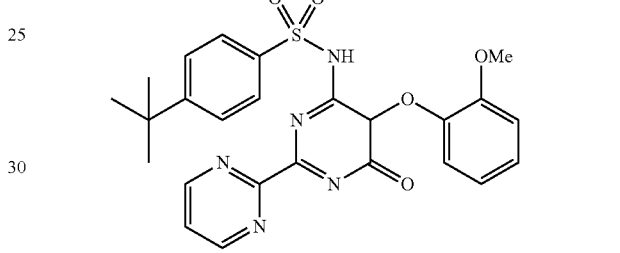

(Ib)

is a known drawback of the so called first-generation process (see Harrington et. al., Organic Process Research & Development 2002, Vol. 6, 120-124).

The control of impurities is currently a critical issue to the drug manufacturer, who is required by the regulatory authorities to include in the submission of a marketing authorization for a drug product, analytical data which demonstrate that impurities are absent from the active pharmaceutical ingredient (API) at the time of manufacture, or are present at acceptable levels.

Therefore, the formation of any impurities and particularly, in the present case, the formation of the above-identified dimer and pyrimidinone impurities, requires costly and laborious separation steps to isolate a pharmaceutically suitable Bosentan Monohydrate. For example, according to the above-cited Harrington's article, at least two final product crystallizations from methanol-isopropyl acetate are required to lower said impurities levels.

In order to avoid the formation of the undesired dimer impurity, in Hoffmann La-Roche EP 1254121 a variation of the final step was performed by using, instead of sodium ethylene glycol, a mono-protected ethylene glycol, such as (mono) tert-butyl ether protected ethylene glycol. After coupling tert-butyl ether protected ethylene glycol with the 6-chloro sulfonamide intermediate, tert-butyl group is hydrolyzed with formic acid to obtain a formyl derivative, which is removed with sodium hydroxide (NaOH) to yield Bosentan.

As follows from the above mentioned prior art, there is a need for a process to prepare Bosentan Monohydrate in a pure form by an effective method, which is applicable to large-scale industrial production.

SUMMARY OF THE INVENTION

The present inventors have identified a practical alternative method, which allows to easily discharging undesired dimer impurity and pyrimidinone impurity and provides an efficient process for preparing Bosentan Monohydrate, acceptable for administration to human and susceptible of use on industrial scale. The method of the present invention comprises the use of Bosentan sodium salt, obtained in a previously undisclosed ethylene glycol solvate form.

In a first aspect, the present invention therefore relates to a novel ethylene glycol solvate of Bosentan sodium salt, which can be employed in the production of a pure form of Bosentan Monohydrate.

In a particular aspect, the present invention relates to a crystalline form of a novel ethylene glycol solvate of the Bosentan sodium salt.

In a more particular aspect, the present invention relates to the crystalline form of the novel ethylene glycol solvate of Bosentan sodium salt as characterized by the XRPD pattern of FIG. 1.

In yet another aspect, provided herein is pure Bosentan sodium salt, namely Bosentan sodium salt substantially free of the dimer and pyrimidone impurities.

Another aspect of the present invention provides a process for preparing a novel ethylene glycol solvate of Bosentan sodium salt.

In another aspect, the present invention further encompasses the use of Bosentan sodium salt as an ethylene glycol solvate for the preparation of Bosentan Monohydrate.

In another aspect, the present invention further provides a process for preparing Bosentan Monohydrate with high purity, by using Bosentan sodium salt ethylene glycol solvate of the present invention.

DETAILED DESCRIPTION OF THE INVENTION

In a first aspect, the present invention relates to a novel ethylene glycol solvate of Bosentan sodium salt of formula (IV)

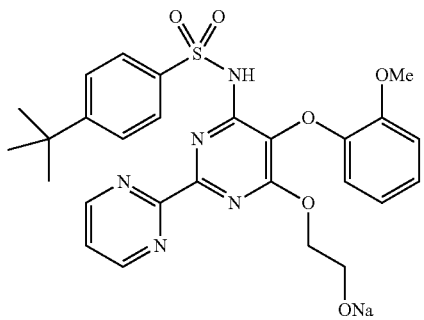

Ethylene glycol solvate of Bosentan sodium salt of formula (IV) can be employed in the production of a pure form of Bosentan Monohydrate of formula (I).

In a particular aspect, the present invention relates to the crystalline form of a novel ethylene glycol solvate of Bosentan sodium salt, having a XRPD comprising peaks expressed at the following degrees two-theta values: 6.4, 8.4, 9.0, 9.9, 12.0, 18.2 and 20.4, plus or minus 0.2 degrees.

Figure 1:
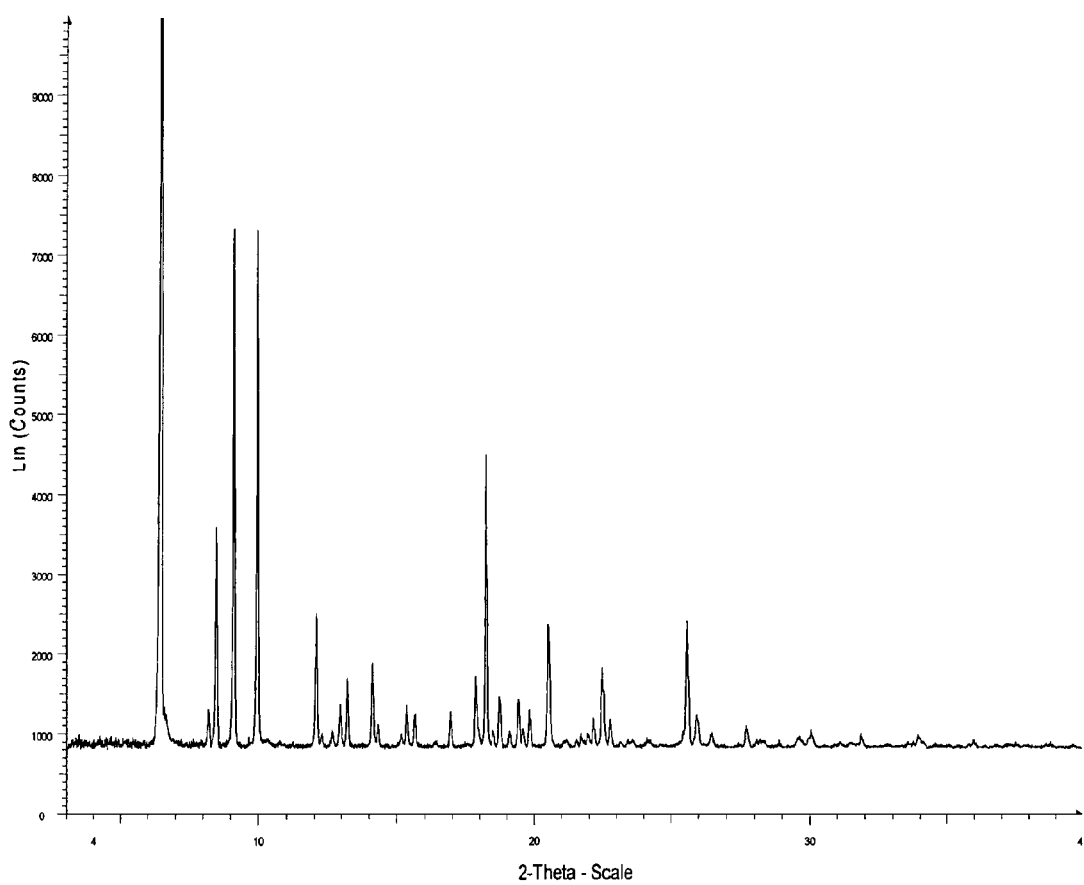
FIG. 1 is a characteristic X-ray Powder Diffraction (XRPD) pattern for Bosentan sodium salt ethylene glycol solvate.

In a more particular aspect, the present invention relates to the crystalline form of a novel ethylene glycol solvate of the crude Bosentan sodium salt as characterized by the XRPD pattern of FIG. 1.

In yet another aspect, provided herein is pure Bosentan sodium salt, namely Bosentan sodium salt substantially free of dimer and pyrimidone impurities.

Figure 2:
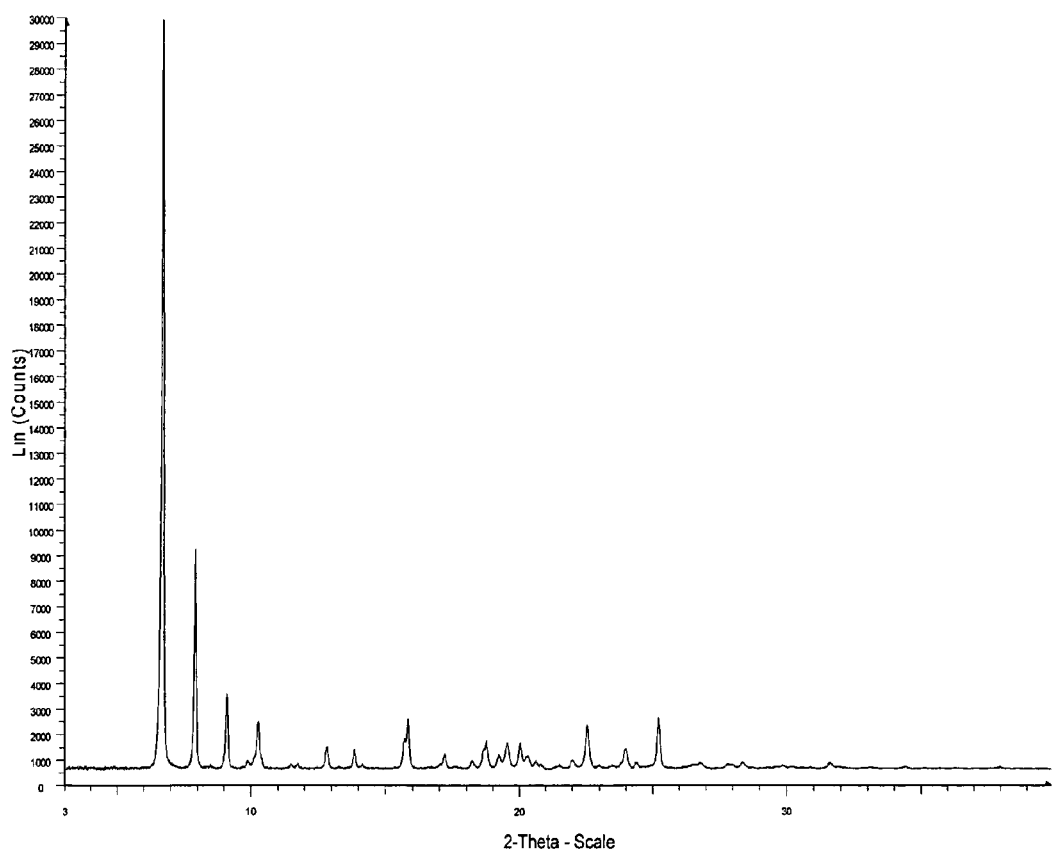
FIG. 2 is a characteristic X-ray Powder Diffraction (XRPD) pattern for the pure Bosentan sodium salt.

In a still another aspect, provided herein is pure Bosentan sodium salt having a XRPD comprising peaks expressed at the following degrees two-theta values: 6.6, 7.8, 9.0, 10.2 and 25.2, plus or minus 0.2 degrees, in particular Bosentan sodium salt as characterized by the XRPD pattern of FIG. 2.

As used herein, "pure Bosentan sodium salt" means Bosentan sodium salt substantially free of dimer and pyrimidone impurities, namely it refers to Bosentan sodium salt wherein the total content of such impurities is less than about 0.3% w/w as measured by high performance liquid chromatography ("HPLC"), and each individual impurity is less than about 0.15% w/w as measured by HPLC; more specifically the total content of such impurities is less than about 0.2% w/w as measured by HPLC, and each individual impurity is less than about 0.1% w/w as measured by HPLC; still more specifically the total content of such impurities is less than about 0.1% w/w as measured by HPLC, each individual impurity is less than about 0.05% w/w as measured by HPLC; and most specifically essentially free of such impurities.

Another aspect of the present invention provides a process for preparing a novel ethylene glycol solvate of Bosentan sodium salt of formula (IV)

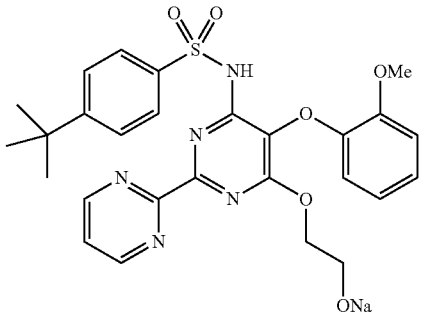

which comprises
a) coupling 4-tert-butyl-N-[6-chloro-5-(2-methoxy-phenoxy)-2-(2-pyrimidinyl)-pyrimidin-4-yl]benzenesulfonamide potassium salt of formula (II)

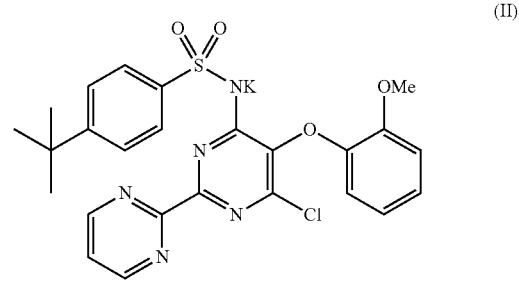

with sodium ethylene glycolate of formula (III)

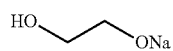
(III)

operating in ethylene glycol as a solvent, heating the reaction mixture at a temperature ranging from 65° C. to 75° C.;
b) allowing or promoting the precipitation of the desired Bosentan sodium salt as ethylene glycol solvate; and
c) recovering it from the reaction mixture.

In another aspect, the present invention further encompasses the use of Bosentan sodium salt ethylene glycol solvate as defined above for the preparation of Bosentan Monohydrate of formula (I).

In another aspect, the present invention further provides a process for preparing Bosentan Monohydrate of formula (I), by using the Bosentan sodium ethylene glycol solvate of the present invention.

In another aspect, the present invention further provides a process for preparing Bosentan Monohydrate of formula (I)

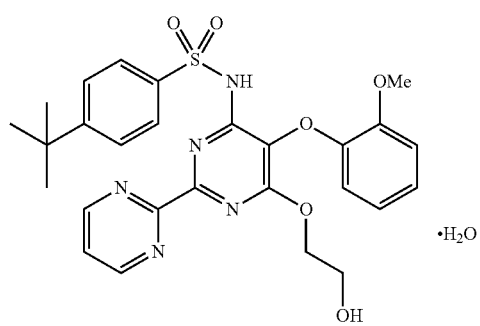
(I)

which comprises:
a) coupling 4-tert-butyl-N-[6-chloro-5-(2-methoxy-phenoxy)-2-(2-pyrimidinyl)-pyrimidin-4-yl]-benzenesulfonamide potassium salt of formula (II)

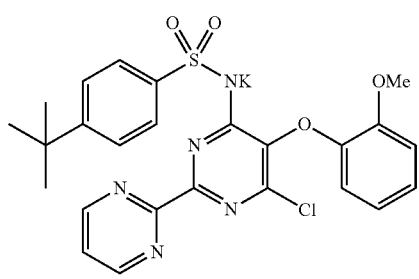
(II)

with sodium ethylene glycolate of formula (III)

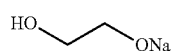
(III)

operating in ethylene glycol as a solvent, heating the reaction mixture at a temperature ranging from 65° C. to 75° C. to give Bosentan sodium salt of formula (IV) as a ethylene glycol solvate

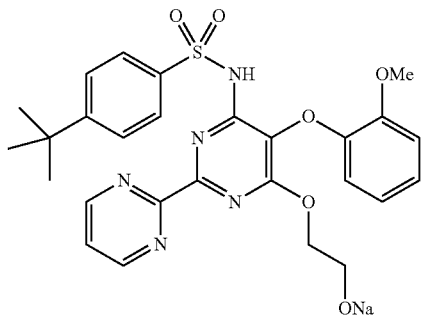
(IV)

b) allowing or promoting the precipitation Bosentan sodium salt as ethylene glycol solvate from the reaction mixture;
c) recovering Bosentan sodium salt as ethylene glycol solvate from the reaction mixture;
d) providing a solution of Bosentan sodium salt ethylene glycol solvate of formula (IV) in ethanol alone or in a mixture with acetone and/or cyclohexane at a temperature ranging from 65° C. to 75° C.;
e) allowing or promoting Bosentan sodium salt of formula (IV) to crystallize from the solution;
f) recovering Bosentan sodium salt of formula (IV); and
g) converting Bosentan sodium salt into Bosentan Monohydrate of formula (I); characterized in that the dimer impurity of formula (Ia) and the pyrimidinone impurity of formula (Ib) as defined above, which can be generated when performing reaction steps a) to d), remain in the supernatant solution when Bosentan sodium salt is obtained under reaction steps e) and f); namely Bosentan sodium salt recovered under step f) is substantially free of said impurities.

Figure 3:
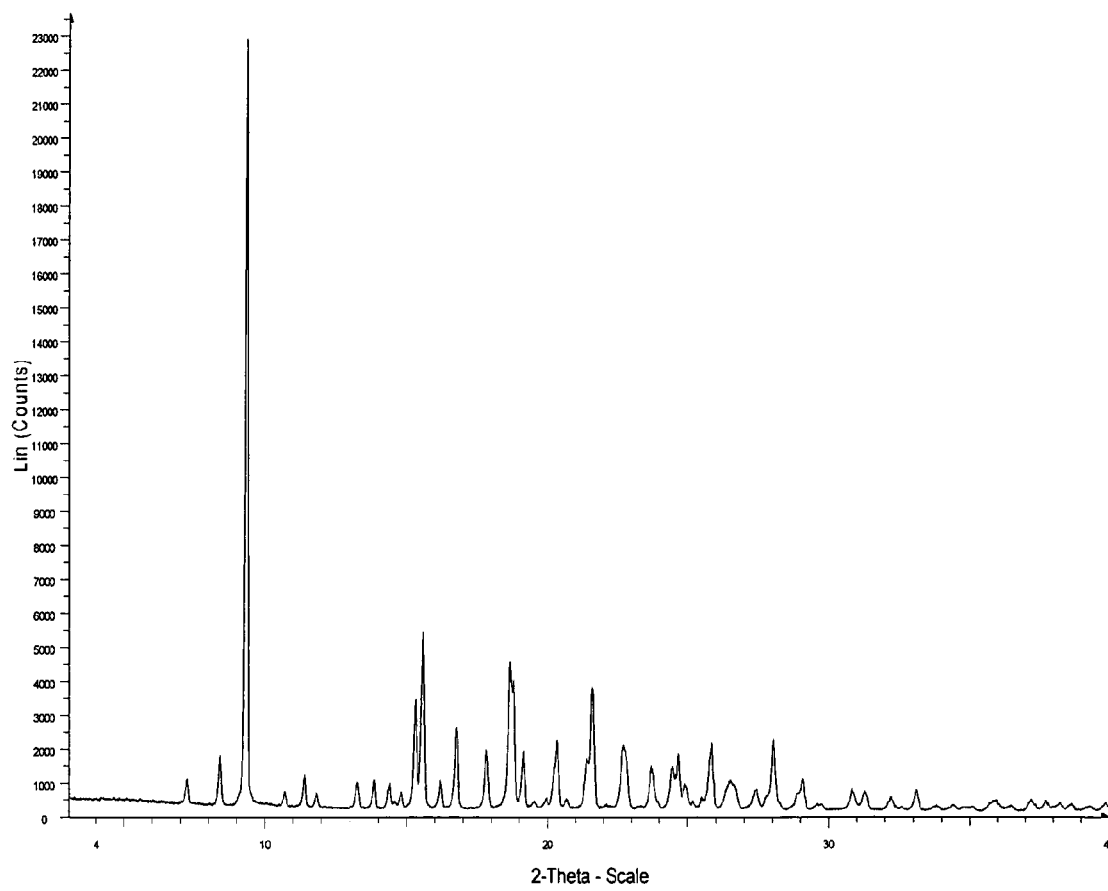
FIG. 3 is a characteristic X-ray Powder Diffraction (XRPD) pattern for Bosentan Monohydrate.

Bosentan Monohydrate of formula (I) obtained according to the process of the present invention is in a crystalline form, having an XRDP as reported in FIG. 3., whose characterizing peaks match with Bosentan Monohydrate cell data as described in Harada et al., Bioorganic & Medicinal Chemistry, Elsevier Science ltd., vol. 9, 1 Jan. 2001, 2955-2968, page 2967, top of second column.

As used herein the term "solvate" means a crystal form which includes, as part of its crystalline structure, stoichiometric or non-stoichiometric amount of solvent from which the crystal has been precipitated.

All reagents are commercially available and used without further purification unless indicated otherwise in the present specification.

According to the present invention, the coupling according to step a) can be carried out heating the reaction mixture at a temperature ranging from 65° C. to 75° C., preferably from 68° C. to 72° C., and maintaining said temperature until formation of Bosentan sodium salt ethylene glycol solvate is completed.

Typically, the precipitation of Bosentan sodium salt as ethylene glycol solvate under step b) can be spontaneously initiated in a reaction container without the help of an external aid; alternatively, the precipitation of Bosentan sodium salt as ethylene glycol solvate under step b) can be initiated or promoted by seeding the reaction mixture with "seeds" of Bosentan sodium salt as ethylene glycol solvate.

Typically, the recovery of the Bosentan sodium salt as ethylene glycol solvate under step c) is carried out by any method known to one of skill in the art such as filtration, filtration under vacuum, decantation, centrifugation, or a combination thereof, preferably by filtration.

Preferably, Bosentan sodium salt ethylene glycol solvate is collected as a wet cake, wherein residual ethylene glycol is about 20% to about 40%.

As already told before, Bosentan sodium salt ethylene glycol solvate obtained according to the process of the present invention is stable, consistently reproducible and is particularly suitable for bulk preparation and handling. Moreover, Bosentan sodium salt ethylene glycol solvate enhances management of the above-identified process impurities and it is a useful intermediate in the preparation of Bosentan Monohydrate in high purity.

According of the present invention, the solution of Bosentan sodium salt ethylene glycol solvate under step d) is provided by dissolving Bosentan sodium salt ethylene glycol solvate as obtained according to step c) in ethanol alone or in a mixture of ethanol with acetone and/or cyclohexane as a solvent, preferably in a mixture of ethanol and acetone, at a temperature ranging from 65° C. to 75° C., preferably from 68° C. to 72° C., for a time of about 2 hours, particularly in a mixture of ethanol, acetone and cyclohexane. In a preferred aspect, the solution of Bosentan sodium salt ethylene glycol solvate is provided by dissolving Bosentan sodium salt ethylene glycol solvate as obtained according to step c) in a mixture of ethanol, acetone and cyclohexane as a solvent wherein, preferably, at least about 80%, more preferably at least about 85%, suitably at least about 90% per weight of the solvent is ethanol.

According of the present invention, the precipitation of the crystalline pure form of Bosentan sodium salt according to step e) can be spontaneously initiated in a reaction container without the help of an external aid, or alternatively can be initiated or promoted by seeding the reaction mixture with "seeds" of crystals of pure Bosentan sodium salt, in order to induce crystallization of pure form of Bosentan sodium salt.

In a preferred aspect, the "seeds" of crystals of pure Bosentan sodium salt are charged before adding the solvent.

According to the present invention, the recovering of the crystalline pure form of Bosentan sodium salt under step f) is carried out by separating the product from the supernatant solution. Typically, the recovering of the crystalline pure form of Bosentan sodium salt is carried out by any method known to one of skill in the art such as filtration, filtration under vacuum, decantation, centrifugation, or a combination thereof. In a preferred embodiment, the crystalline pure form of Bosentan sodium salt is recovered by filtration or centrifugation.

If desired, the crystalline pure form of Bosentan sodium salt obtained by above process may be further dried to lower residual solvents.

According to the present invention the conversion of the crystalline pure form of Bosentan sodium salt into Bosentan Monohydrate of step g) can be carried out by processes known in the art, for example following the procedure described in EP 2072503. Alternatively, the conversion of the crystalline pure form of Bosentan sodium salt into Bosentan Monohydrate can be carried out, for example, in a mixture of acetone/water 1:1, adjusting pH to 4-5 by addition of hydrochloric acid.

The compound of formula (II) is known and can be prepared according to prior art methods, for example following the procedure described in EP 1254121.

The compound of formula (III) is a known compound and can be prepared according to prior art methods, for example following the procedure described in EP 526708.

Alternatively, the compound of formula (III) as defined above can be prepared by reacting sodium methoxide ($CH_3ONa$) with ethylene glycol.

According to another aspect of the present invention, the preparation of Bosentan sodium salt as ethylene glycol solvate can be carried out by a process which comprises adding 4-tert-butyl-N-[6-chloro-5-(2-methoxy-phenoxy)-2-(2-pyrimidinyl)-pyrimidin-4-yl]-benzenesulfonamide potassium salt of formula (II) directly to the reaction mixture containing the compound of formula (III) obtained by contacting sodium methoxide ($CH_3ONa$) with ethylene glycol.

In another aspect, the present invention further encompasses the use of Bosentan sodium salt ethylene glycol solvate as defined above for the preparation of Bosentan Monohydrate of formula (I).

A particular advantage of the present invention is that the formation of Bosentan sodium salt as an ethylene glycol solvate provides, unexpectedly, the possibility to dissolve completely the same in the solvent together with the undesired above-identified impurities, and hence to induce the precipitation of the insoluble pure Bosentan sodium salt from the reaction mixture, and leaving said impurities in the supernatant solution.

The following examples illustrate the invention.

EXAMPLE 1

Preparation of Bosentan Sodium Salt Ethylene Glycol Solvate 86.3 g (153 mmol) of 4-tert-butyl-N-[6-chloro-5-(2-methoxy-phenoxy)-2-(2-pyrimidinyl)-pyrimidin-4-yl]-benzenesulfonamide potassium salt (II) were added to a solution of sodium ethylene glycolate (10 eq) in ethylene glycol (1650 g). The mixture was allowed to heat to 70° C. for about 15 hours. When the reaction was completed, the mixture was cooled down to 50° C. and Bosentan sodium salt ethylene glycol solvate was seeded providing precipitation. Chilling to room temperature was continued and the mixture was further aged at that temperature for 3 hours before collecting the solid by filtration. 124.7 g of the desired crude product were obtained as wet material.

EXAMPLE 2

Preparation of Bosentan Sodium Salt Ethylene Glycol Solvate 19.4 g (358.5 mmol) of sodium methoxide in methanol were added to ethylene glycol (381 g). The mixture was heated to 85° C. and methanol was distilled off under reduced pressure. The mixture was allowed to chill to room temperature and then 20.2 g (35.8 mmol) of 4-tert-butyl-N-[6-chloro-5-(2-methoxy-phenoxy)-2-(2-pyrimidinyl)-pyrimidin-4-yl]-benzenesulfonamide potassium salt (II) were added.

The mixture was allowed to heat to 70° C. for about 15 hours. When the reaction was completed, the mixture was cooled down to 50° C., 17.4 g of dem. water were charged and Bosentan sodium salt ethylene glycol solvate was seeded providing precipitation. Chilling to room temperature was continued and the mixture was further aged at that temperature for 3 hours before collecting the solid by filtration. 26.4 g of the desired crude product were obtained as wet material.

EXAMPLE 3

Preparation of Pure Bosentan Sodium Salt Substantially Free of Dimer and Pyrimidinone Impurities.

To a mixture of ethanol 92% acetone 5% and cyclohexane 3% (300 g) pure crystalline Bosentan sodium seeds were added. Stirring was started and 124.7 g of wet crude Bosentan sodium salt ethylene glycol solvate obtained in Example 1 were given to the suspension. The mixture was heated to 70° C. for about 2 hours and then cooled at 20° C. in about 1 hour. This procedure was repeated and finally the suspension was aged at about 20° C. for additional 5 hours. The solid was filtered and the cake washed with a mixture of ethanol 92% acetone 5% and cyclohexane 3% (115 g). 71.2 g of the pure crystalline Bosentan sodium salt were obtained after drying at 50° C. in vacuo overnight.

Dimer impurity content 0.04% measured by HPLC
Pyrimidinone impurity content 0.05% measured by HPLC

EXAMPLE 4

Preparation of Bosentan Monohydrate 40 g of Bosentan sodium salt were dissolved in acetone (353 g) and 8.48 g of hydrochloridric acid were added. Precipitated salts were filtered off and the clear solution was concentrated by distillation to a residual volume of 190 mL. The mixture was cooled to 55° C. and demineralized water (58 g) was slowly dropped keeping the temperature at 55° C. After 2 hours aging the temperature was decreased to 20° C. in 1 hour and stirred for additional 2 hours at that temperature. The precipitated solid was collected by filtration and the cake was washed with water-acetone 1:1 (38 g). 39.4 g of the desired product were obtained after drying in vacuo.

The invention claimed is:

1. A crystalline form of Bosentan sodium salt of formula (IV)

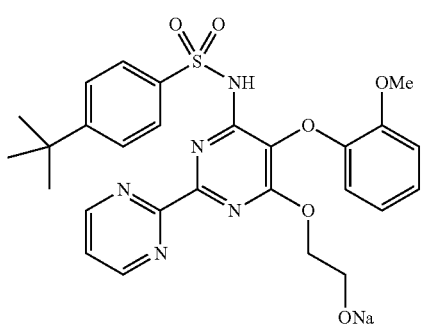

(IV)

wherein the crystalline form comprises, as part of its crystalline structure, stoichiometric or non-stoichiometric amounts of ethylene glycol.

2. The crystalline form of ethylene glycol solvate of Bosentan sodium salt according to claim 1, having a XRPD comprising peaks expressed at the following degrees two-theta values: 6.4, 8.4, 9.0, 9.9, 12.0, 18.2 and 20.4, plus or minus 0.2 degrees.

3. A process for preparing Bosentan sodium salt as ethylene glycol solvate according to claim 1 comprising
a) coupling 4-tert-butyl-N-[6-chloro-5-(2-methoxy-phenoxy)-2-(2-pyrimidin-yl)-pyrimidin-4-yl]benzenesulfonamide potassium salt of formula (II)

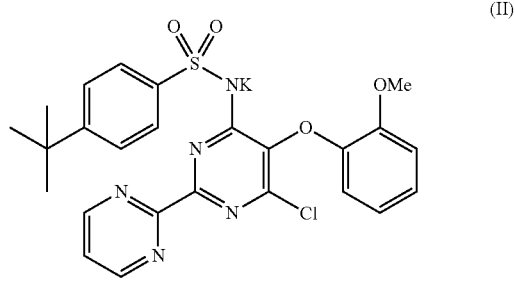

(II)

with sodium ethylene glycolate of formula (III)

(III)

operating in ethylene glycol as a solvent, heating the reaction mixture at a temperature ranging from 65° C. to 75° C.;
b) allowing or promoting the precipitation of the desired Bosentan sodium salt as ethylene glycol solvate; and
c) recovering said Bosentan sodium salt ethylene glycol solvate from the reaction mixture.

4. The process according to claim 3, wherein Bosentan sodium salt ethylene glycol solvate is collected as a wet cake, wherein residual ethylene glycol is about 20% to about 40%.

5. The process for preparing Bosentan sodium salt as ethylene glycol solvate according to claim 3, wherein the compound of formula (III) is obtained by reacting sodium methoxide ($CH_3ONa$) with ethylene glycol.

6. A method for preparing Bosentan Monohydrate of formula I with the crystalline form of ethylene glycol solvate of Bosentan sodium salt according to claim 1

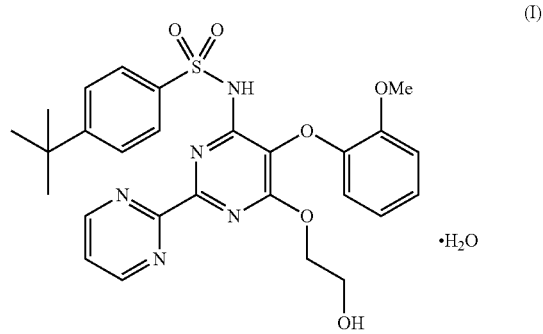

(I)

comprising solubilizing the crystalline form of ethylene glycol solvate of Bosentan sodium salt in a mixture of acetone/water 1:1 adjusting the pH to 4-5 by the addition of hydrochloric acid and obtaining Bosentan Monohydrate.

7. A pure Bosentan sodium salt of formula (IV)

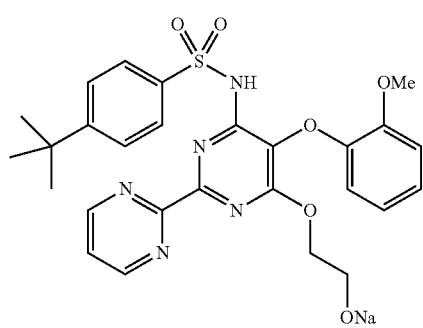
(IV)

comprising dimer impurity of formula (Ia) and pyrimidine impurity of formula (Ib)

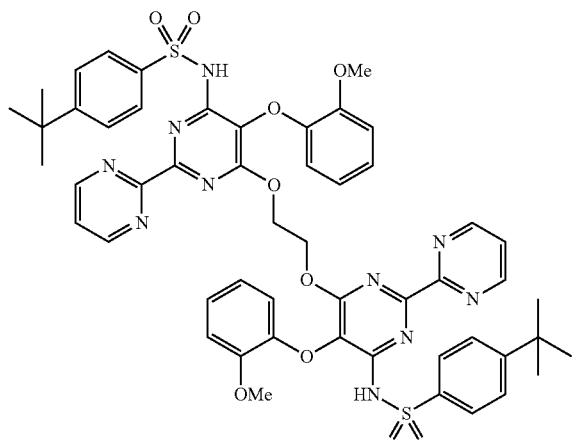
(Ia)

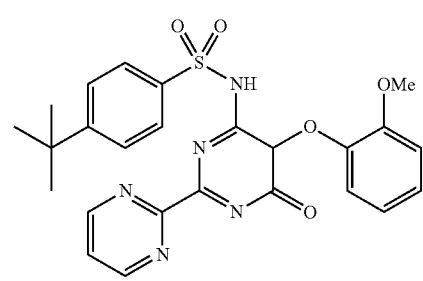
(Ib)

wherein the total content of such impurities is less than 0.3% as measured by high performance liquid chromatography ("HPLC").

8. The Bosentan sodium salt according to claim 7, wherein the total content of dimer and pyrimidinone impurities is less than about 0.2% as measured by HPLC.

9. The Bosentan sodium salt according to claim 8, wherein the total content of dimer and pyrimidinone impurities is less than about 0.1% as measured by HPLC.

10. The Bosentan sodium salt of formula (IV) according to claim 7, having a XRPD comprising peaks expressed at the following degrees two-theta values 6.6, 7.8, 9.0, 10.2 and 25.2, plus or minus 0.2 degrees.

11. A process for preparing Bosentan Monohydrate of formula (I)

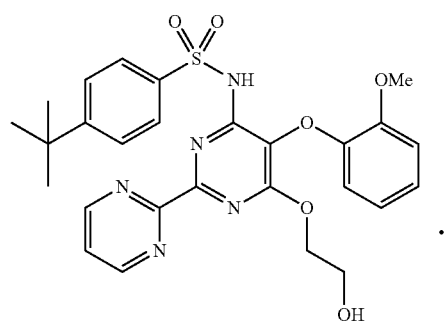
(I)

which comprises
a) coupling 4-tert-butyl-N-[6-chloro-5-(2-methoxyphenoxy)-2-(2-pyrimidinyl)-pyrimidin-4-yl]-benzenesulfonamide potassium salt of formula

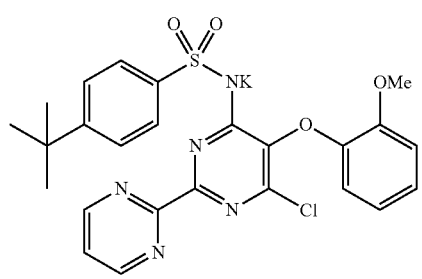
(II)

with sodium ethylene glycolate of formula (III)

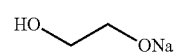
(III)

operating in ethylene glycol as a solvent, heating the reaction mixture at a temperature ranging from 65° C. to 75° C. to give Bosentan sodium salt of formula (IV) as a ethylene solvate

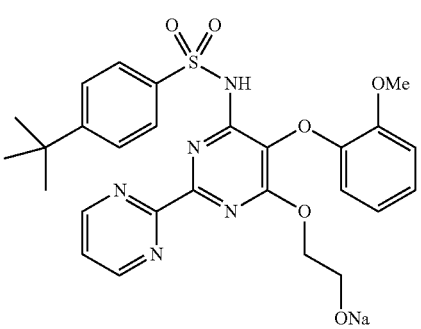
(IV)

b) allowing or promoting the precipitation of Bosentan sodium salt as ethylene glycol solvate from the reaction mixture;

c) recovering Bosentan sodium salt as ethylene glycol solvate from the reaction mixture;
d) providing a solution of Bosentan sodium salt ethylene glycol solvate of formula (IV) in ethanol alone or in a mixture with acetone and/or cyclohexane at a temperature ranging from 65° C. to 75° C.;
e) allowing or promoting pure Bosentan sodium salt of formula (IV) to crystallize from the solution;
f) recovering the pure Bosentan sodium salt of formula (IV); and
g) converting the pure Bosentan sodium salt into Bosentan Monohydrate of formula (I);

wherein the dimer impurity of formula (Ia) and the pyrimidinone impurity of formula (Ib) as defined in claim 7 which can be generated when performing steps a) to d), remain in the supernatant solution when Bosentan sodium salt is obtained under reaction steps e) and f).

12. The process according to claim 11, wherein the solution of Bosentan sodium salt ethylene glycol solvate of step c) is provided by dissolving Bosentan sodium salt ethylene glycol solvate as obtained according to step b) in a mixture of ethanol, acetone and cyclohexane as a solvent, wherein at least 80% per weight of the solvent is ethanol.

13. The process according to claim 11, wherein the precipitation of the crystalline pure form of Bosentan sodium salt according to step e) is initiated or promoted by seeding the reaction mixture with "seeds" of crystals of pure Bosentan sodium salt, in order to induce crystallization of pure form of Bosentan sodium salt.

14. The process according to claim 13, wherein the "seeds" of crystals of pure Bosentan sodium salt are charged before adding the solvent.

* * * * *